United States Patent
Bulow et al.

(10) Patent No.: US 7,341,578 B2
(45) Date of Patent: Mar. 11, 2008

(54) OSTOMY APPLIANCE WITH MULTIPLE OPENINGS FOR PREVENTING FILTER INPUT BLOCKAGE

(75) Inventors: Martin von Bulow, Helsingingoer (DK); Mogens Guldager Kristensen, Helsingoer (DK)

(73) Assignee: Coloplast A/S, Humlebaek (DK)

(*) Notice: Subject to any disclaimer, the term of this patent is extended or adjusted under 35 U.S.C. 154(b) by 0 days.

(21) Appl. No.: 10/488,541

(22) PCT Filed: Sep. 5, 2002

(86) PCT No.: PCT/DK02/00577

§ 371 (c)(1),
(2), (4) Date: Mar. 4, 2004

(87) PCT Pub. No.: WO03/020188

PCT Pub. Date: Mar. 13, 2003

(65) Prior Publication Data

US 2005/0070863 A1    Mar. 31, 2005

(30) Foreign Application Priority Data

Sep. 5, 2001    (DK) .............................. 2001 01302

(51) Int. Cl.
*A61F 5/44* (2006.01)

(52) U.S. Cl. ............ 604/333; 604/332; 604/338; 604/339

(58) Field of Classification Search ........ 604/332–337, 604/327, 277; 600/32; 128/887
See application file for complete search history.

(56) References Cited

U.S. PATENT DOCUMENTS

| 4,367,732 A | 1/1983 | Poulsen et al. ............. 128/156 |
| 4,387,712 A | 6/1983 | Briggs et al. ................ 604/333 |
| 4,427,425 A * | 1/1984 | Briggs et al. .................. 96/12 |
| 4,439,191 A * | 3/1984 | Hogan ........................ 604/332 |
| 4,938,750 A | 7/1990 | Leise, Jr. .................... 604/333 |
| 5,051,259 A | 9/1991 | Olsen et al. ................. 424/443 |
| 5,342,434 A | 8/1994 | Wu ............................... 96/13 |
| 5,690,623 A * | 11/1997 | Lenz et al. .................. 604/333 |
| 5,714,225 A | 2/1998 | Hansen et al. .............. 428/114 |
| 5,733,271 A | 3/1998 | Bjørn ......................... 604/333 |
| 5,800,415 A | 9/1998 | Olsen ......................... 604/336 |

FOREIGN PATENT DOCUMENTS

| DK | 199800493 | 12/1998 |
| EP | 0235928 A1 * | 1/1987 |
| EP | 0 235 928 | 9/1987 |
| EP | 0 443 728 | 8/1991 |
| GB | 2 083 760 | 3/1982 |

(Continued)

*Primary Examiner*—Tatyana Zalukaeva
*Assistant Examiner*—Melanie J. Hand
(74) *Attorney, Agent, or Firm*—Jacobson Holman PLLC

(57) ABSTRACT

An ostomy appliance having a vent covered by a filter. Gas inlet and outlet openings are provided that are in communication with a filter body and arranged so that in use gas flows through the filter body from the inlet opening to the outlet opening. The gas inlet opening communicates with at least two separate and independent closed pathways that have respective inlet openings separated from one another. Each of the pathway outlet openings is covered by a microporous membrane showing improved resistance against blocking of the inlet opening of the filter.

20 Claims, 5 Drawing Sheets

FOREIGN PATENT DOCUMENTS

| | | |
|---|---|---|
| WO | 91/01118 | 2/1991 |
| WO | 91/01119 | 2/1991 |
| WO | 94/18919 | 9/1994 |
| WO | 98/44880 | 10/1998 |
| WO | WO 98/44880 A1 * | 10/1998 |
| WO | 99/66859 | 12/1999 |

* cited by examiner

OSTOMY APPLIANCE WITH MULTIPLE OPENINGS FOR PREVENTING FILTER INPUT BLOCKAGE

This is a nationalization of PCT/DK02/00577 filed Sep. 5, 2002 and published in English.

BACKGROUND OF THE INVENTION

1. Field of the Invention

The present invention relates to an ostomy appliance comprising a deodorising filter, in particular ostomy bags, and to a filter device.

In connection with surgery for a number of diseases in the gastrointestinal tract a consequence is, in many cases, that the patient is left with a stoma such as a colostomy, an ileostomy or an urostomy in the abdominal wall for the discharge of the effluents or waste products of the body, which are conveyed through the colon, the ileum or the ureter. The discharge of visceral contents including intestinal gases cannot be regulated at will, and for that purpose the opening may be closed with a closure means, e.g. a tampon or a magnetic closure, or the patient will have to rely on an appliance to collect the material emerging from such opening in the form of a receiving bag which is later emptied and/or discarded at suitable times.

Ostomy appliances are well known. Such appliances may be two-piece or one-piece appliances. In both types of appliances, an adhesive wafer is attached to the wearer's skin. In case of a one-piece appliance, a receiving member or bag is attached to the adhesive wafer. In case of a two-piece appliance, the adhesive wafer forms part of a body side member and a receiving bag is attached releasably to the body side ostomy member for receiving exudates from the stoma.

When using one-piece appliances, the whole appliance, including the adhesive skin barrier securing the appliance to the skin is normally removed and replaced by afresh appliance. When using two-piece appliances, the body side member is left in place up to several days, and only the receiving bag attached to the body side member is replaced.

The discharge of flatus, measured in volume, may exceed the discharge of solid and liquid faecal matter by many hundred percent and therefore there is usually the need for the continuous or frequent venting of the intestine or the collecting bag. Normally the outflowing flatus is deodorised with a suitable filter. Commonly the active filter is powdered active carbon, which absorbs $H_2S$ being the principal component of the smell of flatus.

2. Description of the Related Art

Various constructions of filters for ostomy appliances are known. In the state of the art, the filters are designed so as to obtain a high security of deodorisation of the flatus by securing that there is no by-pass by which the flatus may circumvent the filter, and some measures have been discussed with respect to obtaining a better security against blocking of the inlet of the filter by solid discharged visceral content. When the inlet opening of the filter is blocked, the gas discharged into the ostomy appliance cause ballooning of the bag which is highly undesirable for several reasons. Ballooning will be embarrassing for the user as the bag will bulge and there is an increased risk of leakage which is unacceptable for the user.

European Patent No. 0 235 928 discloses that a filter may be rendered suitable for use with ileostomy equipment when the filter wall adapted to face the source of intestinal gas is covered by a layer of sheet material, preferably plastic sheet material connected to the filter walls and inside the periphery of this connection, provided with openings for the passage of intestinal gas. Conveniently these openings, which may for instance be slits of a width of 0.5-1 mm and a length of a few millimeters, may be situated outside the peripheral edge of the filter body. However, such slits may open if the pressure is high giving free flow of gas and liquid through the layer of sheet material. In the alternative, it is proposed to provide the filter housing on the surface adapted to face the source of intestinal gas with a layer of liquid-absorbing material. The area of the absorbent material is conveniently the same as the area of the filter body or somewhat larger but the positioning on the wall in question should be such that the absorbent material does not cover the inlet opening for intestinal gas to be deodorised since saturation of the liquid-absorbing material with liquid might prevent the passage of the intestinal gas. Furthermore, it is proposed to render the filter particularly efficient for ileostomy equipment by providing it both with a covering sheet and an absorbent layer of material.

EP patent No. 0 443 728 B1 discloses a bag for receiving discharge from the human body comprising a filter and an intervening membrane covering the inlet opening of the filter, said intervening membrane being gas permeable but not liquid permeable. It is mentioned that the membrane may comprise a polyester film bonded to a PTFE film and that such membrane showed no leakage of water. There is no indication of security against leaking when exposed for discharge from an ileostomy or liquids from a colostomy.

U.S. Pat. No. 5,342,434 discloses a gas permeable coated porous membrane having enhanced oleophobic and hydrophobic properties. The membrane may be a PTFE membrane coated with a diisocyanate coating and the membranes are stated to be useful in waterproof, breathable fabrics and gas vents or filters that protect electronic equipment used in or near automotive engines. Although other useful applications are stated to be medical devices where venting filters are needed, this reference is silent with respect to safety against wetting of filters for ostomy appliances by the visceral contents of an ostomy collection bag which contents has a very complex composition of biologically active compounds from the digestive system.

U.S. Pat. No. 4,387,712 discloses a surgical collection bag having two opposed walls secured together by a perimeter weld, said bag having a vent and said bag also having welds inside the bag defining together with the perimeter weld a pathway through which gases can flow from the interior of the bag to the vent. The pathway includes one or more vents through which gases must pass before reaching the vent.

Published International Patent Application WO 98/44880 discloses a filter for covering a vent of an ostomy appliance, said filter comprising an elongated, substantially flat filter body of a porous filter material interposed between gas and liquid impervious walls which are sealed to the body along its longitudinal side edges; gas inlet and outlet openings being provided in communication with the filter material adjacent to its respective longitudinal end regions, wherein both of the gas and liquid impervious walls are sealed to the upper and lower surfaces of the filter body, wherein the inlet opening is covered by a hydrophobic sheet, wherein the inlet opening is covered with a microporous oleophobic membrane and wherein a foam material is covering the inlet opening of the vent. It is disclosed that there may a compartment functioning as an inlet pathway, which pathway may have one or more openings for letting in gas from the interior of the ostomy appliance. Such arrangement shows improved resistance against wetting and blocking of the filter caused by humidity or other liquid constituents of the visceral contents of an ostomy collection bag and, at the same time, shows improved resistance against clogging of the filter.

However, it has been found that, especially for ostomates having an ileostomy and especially at night when they turn in bed, there is a risk of directly pressing faeces in the receiving bag against the inlet opening(s) of the filter and that the pressure may be sufficiently high to force the front of visceral material through a foam material covering a single inlet opening of the vent and past the inlet opening of the filter to cause a blocking of a microporous oleophobic membrane covering the inlet opening of the vent as the one or all of the passage way(s) communicate with one and the same compartment. This applies to both U.S. Pat. No. 4,387,712 and Published International Patent Application WO 98/44880 which both discloses only one inlet opening to the filter.

Thus, there is still a need of measures for effectively preventing blocking of the inlet opening of filters of ostomy appliances.

It has now been found that it is possible to reduce the risk of blocking of the inlet opening of filters of ostomy appliances in a manner that almost eliminates the risk and, at the same time, is simple to carry out in industrial practice.

Thus, it has been found that the above drawbacks can be avoided by improving the form of the passage to the inlet opening of the filter.

SUMMARY OF THE INVENTION

The invention relates in a first aspect to an ostomy appliance comprising a front wall and a rear wall of flexible material forming a bag, the rear wall having an opening into the bag by which waste material can enter the bag and one of the walls has one or more vents through which gas may escape from the bag and having a filter covering said vent wherein gas inlet and outlet openings are provided in communication with a filter body, the arrangement being so that in use gas flows through the filter from the inlet opening to the outlet opening, such gas flow being confined to said filter body.

The invention furthermore relates to a deodorising filter device especially apt for covering a vent of an ostomy appliance or the like, which deodorising filter device comprises a filter having a filter body of a porous filter material interposed between gas and liquid impervious walls which are sealed to the body along its edges; gas inlet and outlet openings being provided in communication with the filter body material, wherein both of the gas and liquid impervious walls are sealed to the upper and lower surfaces of the filter body, the arrangement being so that in use gas flows through the filter from the inlet opening to the outlet opening, such gas flow being confined to said filter body wherein the gas inlet opening to the filter is provided with at least two separate and independent closed pathways having separated inlet openings communicating with the bag and outlet openings communicating with the inlet opening of the filter.

BRIEF DESCRIPTION OF THE DRAWINGS

The invention is disclosed more in detail with reference to the following drawings.

DETAILED DESCRIPTION OF THE PRESENT INVENTION

Figures 1, 1A:
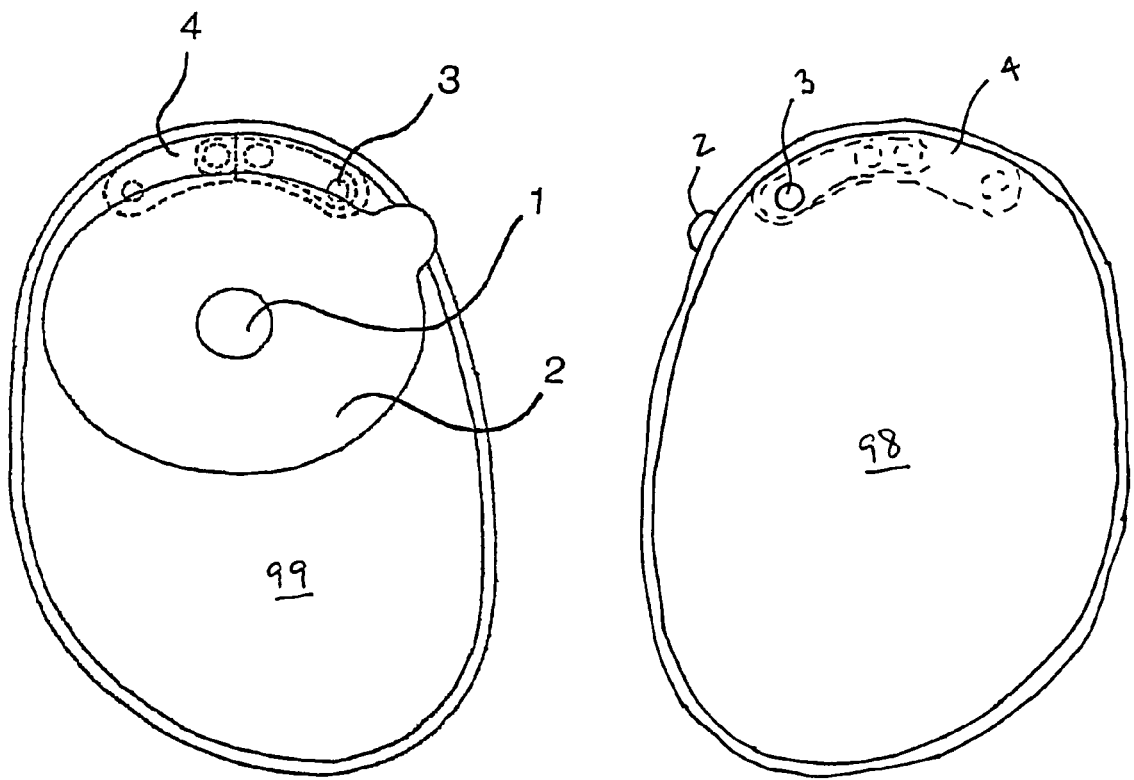
FIG. 1 shows an embodiment of an ostomy appliance of the present invention from the side facing the user.
FIG. 1A is a view of the ostomy appliance of FIG. 1 from the side facing away from the user.

The present invention relates to an ostomy appliance comprising a front wall and a rear wall of flexible material forming a bag, the rear wall having an opening into the bag by which waste material can enter the bag and one of the walls has one or more vents through which gas may escape from the bag and having a filter covering said vent wherein gas inlet and outlet openings are provided in communication with a filter body, the arrangement being so that in use gas flows through the filter from the inlet opening to the outlet opening, such gas flow being confined to said filter body, wherein the gas inlet opening to the filter is provided with at least two separate and independent closed pathways having separated inlet openings communicating with the bag and separate and independent outlet openings communicating with the inlet opening of the filter and wherein each of the outlet openings of the separate pathways are covered by a microporous membrane.

In an alternative embodiment, the filter has more than one inlet opening in which case microporous membranes may cover these openings instead.

The risk of blocking of the inlet opening of the filter is significantly reduced by the presence of separate and independent closed pathways having separated inlet openings communicating with the interior of the bag and separate outlet openings communicating with the inlet opening of the filter, wherein each of the outlet openings of the separate pathways are covered by a microporous membrane. Thus, material present in a bag of the invention is prevented from entering through one entrance and past the inlet opening of the filter to cause a blocking of other entrances. Furthermore, the presence of separated inlet openings also reduces the probability of material present in the bag entering, at the same time, both pathways leading to the inlet opening of the filter which has been found nearly to eliminate the risk of blocking of the filter by directly pressing the contents of the bag against the inlet opening(s) of the filter e.g. when a lying person turns. e.g. in bed.

The effect of having at least two independent closed pathways having separated inlet openings is improved when the separated inlet openings are spaced a certain distance from each other, a certain effect being found already at a distance of at least 15 mm, the effect increasing with increasing distance until a distance comparable to the width of the bag is reached. It is preferred, that the distance is at least 50 mm and it is especially preferred, that the distance corresponds to 90% of the width of the bag for which the filter device is intended.

It provides a pronounced effect when the pathways stretch essentially along radii of a circle of reference having a perimeter concentric with the inlet opening of the filter and that the inlet openings of the pathways are spaced at an angle of at least 45 degrees, and it is preferred that the inlet openings are spaced at an angle of at least 90 degrees which ensures that a pressure along one passage will act perpendicular to the other.

It is especially preferred that the inlet openings are spaced at an angle of at least 135 degrees which will be very suitable taking into account the shape of a bag where the filter device is to be placed but angles of up to 180 degrees are considered suitable for the purpose of the present invention.

In a preferred embodiment the invention relates to an ostomy appliance comprising a filter comprising an elongated, substantially flat filter body of a porous filter material and wherein the gas inlet and outlet openings being provided in communication with the filter material adjacent to its respective longitudinal end regions, the arrangement being so that in use gas flows longitudinally through the filter from the inlet opening to the outlet opening, wherein the gas inlet opening to the filter is provided with at least two independent closed pathways having separate inlet openings communicating with the bag and outlet openings communicating with the inlet opening of the filter.

The ostomy receiving bag according to the invention may be adapted for use together with an ostomy body side member (2-piece appliance) wherein the receiving bag is provided with coupling means for releasable securing to matching coupling means placed on the ostomy body side member and wherein the inlet opening is adapted for alignment with a hole of the ostomy body side member for receiving a stoma.

The ostomy receiving bag according to the invention may, as an alternative, be adapted for use directly (1-piece appliance) in which case the bag is provided with an adhesive wafer for securing the receiving bag to the user's skin, said bag and wafer having an inlet opening for receiving a stoma.

The receiving bag itself comprising front and rear walls sealed together along the rim and provided with an inlet opening may be made in analogy with and from materials conventionally used for the preparation of ostomy appliances.

Such materials are suitably films composed of any suitable material which is heat sealable and sufficiently impervious for unpleasant odours such as polyolefin films or combinations of such films, e.g. polyethylene or a coextrudate of polyethylene and polyvinylidene chloride (PVDC).

An ostomy body side member for use together with an ostomy receiving bag according to the invention may be produced from standard materials normally used for preparation of disposable ostomy and wound and incontinence devices.

Thus, the adhesive wafer for a body side member or of a 1-piece ostomy appliance bag according to the invention may be made from a medical grade barrier adhesives known in the such as the formulation being disclosed, for example in U.S. Pat. Nos. 4,367,732, 5,051,259 or 5,714,225. For a 2-piece ostomy appliance according to the invention the body side member and the receiving bag are provided with matching coupling means.

The coupling means for use in connection with the present invention may be any suitable coupling means known per se for coupling of ostomy base plates to ostomy collecting bags, e.g. a mechanical coupling such as matching coupling rings such as the coupling rings disclosed in WO 91/01118 and WO 91/01119 or WO 94/18919 or matching flanges for adhesive connection of the type disclosed in U.S. Pat. No. 5,800,415.

In a further aspect, the invention relates to a deodorising filter device especially apt for covering a vent of an ostomy appliance or the like, which deodorising filter device comprises a filter having a filter body of a porous filter material interposed between gas and liquid impervious walls which are sealed to the body along its edges; gas inlet and outlet openings being provided in communication with the filter body material, wherein both of the gas and liquid impervious walls are sealed to the upper and lower surfaces of the filter body, the arrangement being so that in use gas flows through the filter from the inlet opening to the outlet opening, such gas flow being confined to said filter body wherein the gas inlet opening to the filter is provided with at least two separate and independent closed pathways having separated inlet openings communicating with the bag and separate and independent outlet openings communicating with the inlet opening of the filter and wherein each of the outlet openings of the separate pathways are covered by a microporous membrane.

In a preferred embodiment, the invention relates to a deodorising filter device especially apt for covering a vent of an ostomy appliance or the like, which deodorising filter device comprises a filter having an elongated, substantially flat filter body of a porous filter material interposed between gas and liquid impervious walls which are sealed to the body along its edges, gas inlet and outlet openings being provided in communication with the filter body material adjacent to its respective longitudinal end regions, wherein both of the gas and liquid impervious walls are sealed to the upper and lower surfaces of the filter body, the arrangement being so that in use gas flows longitudinally through the filter from the inlet opening to the outlet opening, such gas flow being confined to said filter body wherein the gas inlet opening to the filter is provided with at least two independent closed pathways having separated inlet openings communicating with the bag and outlet openings communicating with the inlet opening of the filter. Such filter device is very suitable for use in an ostomy appliance.

The independent closed pathways may suitably be formed using one or more further wall(s) made from a sheet material such as foils, woven or non-woven sheet materials which are moisture resistant and may be sealed to the liquid impervious wall comprising the inlet opening of the filter by welding in a corresponding pattern which is readily determined by the skilled in the art.

It is preferred that the inlet of the filter from each pathway is protected by a microporous hydrophobic membrane and that the membrane is covered with a wall defining a space for placing a piece of a foam material, said wall being sealed to the filter with a welding seam crossing the membrane, thereby defining the outlet openings of the two independent closed pathways.

It is preferred that the closed pathways are in the form of elongated canals providing a relatively long distance form the inlet of the pathway to the outlet of the pathway and the inlet of the filter as a very high security is obtained that the material shall not reach the outlet of the canal and block the membrane physically.

In a more preferred embodiment, two separated pieces of foam are placed between two walls of sheet material separated by a welding seam, the outlets of the two independent closed pathways each having a microporous hydrophobic membrane covering the outlet opening of the canal.

In this embodiment, the welding pattern assembling the filter and the pathways are preferably shaped in a manner ensuring that each of the pathways, via the membranes, are communicating with the inlet opening of the filter through a common closed collecting space. This embodiment enables the use of a conventional filter package as a part of a filter device or an ostomy appliance of the invention.

The effect of having at least two independent closed pathways having separated inlet openings is improved when the separated inlet openings are spaced a certain distance from each other, a certain effect being found already at a distance of at least 15 mm, the effect increasing with increasing distance until a distance comparable to the width of the bag for which the filter device is intended is reached. It is preferred, that the distance is at least 50 mm.

For the reasons stated above it is suitable when the pathways stretch along radii of a circle having a perimeter concentric with the inlet opening and that the inlet openings are spaced at an angle of at least 45 degrees, and it is preferred that the inlet openings are spaced at an angle of at least 90 degrees, more preferably at an angle of at least 135 degrees but angles of up to 180 degrees are considered suitable for the purpose of the present invention.

In a further preferred embodiment of a filter device of the invention the membranes covering the outlet openings of the canals comprise a layer of a non-woven material and a layer of an oleophobic PTFE-material which further reduces the risk of wetting of the filter material due to the special composition and aggressiveness of the visceral contents.

It is especially preferred that a foam material is present in the pathways as the foam material further improves the security against blocking of the inlet opening to the filter.

The rejection capacity of the foam material is enhanced when it is rendered hydrophobic which is considered a preferred embodiment.

The foam material is suitably rendered hydrophobic by treatment with a silicone oil being inert to visceral contents.

The foam material is preferably also rendered oleophobic in order to further improve the security against material reaching and blocking of the inlet opening to the filter.

It is preferred that the filter body has a curved shape facilitating the placing inside an ostomy bag.

It is especially advantageous that the top of the filter device and the bag to which it is to be attached have essentially circular shape as this allows for an essentially free placing of the filter device at the most appropriate site in the top of the bag.

The walls of the filter device are preferably of a size leaving an outer rim or flange being apt for securing the filter device to an ostomy appliance. The device may be secured and sealed by any suitable means, e.g. by welding or gluing.

The filter device may be secured to a wall of an ostomy appliance at any suitable step in a conventional process for preparing ostomy appliances and it is within the scope of the invention to produce the inlet hole after securing the filter device, e.g. by cutting or punching a hole through the wall of the appliance and the filter device, this instance referring to the situation when placed inside the bag. If the filter device is placed outside the bag, two holes for the inlets of the two separated pathways would have to be cut.

The front sheet and the backing sheet may be of any suitable material, preferably a material normally used for the preparation of ostomy appliances or a material which may be glued or welded to such materials, e.g. PE, EVA, polyvinylidene chloride, and chlorinated polyethylene or copolymers of PE and EVA or combinations of such foils.

Suitable materials for use as walls for forming the independent closed pathways are sheet materials such as foils, or porous woven or non-woven sheet materials which are moisture resistant and may be united with materials conventionally used in the production of ostomy appliances such as non-woven materials of polyethylene, polypropylene or a polyester.

The filter body may be formed in various ways and may advantageously consist of a compressed foamed plastic impregnated with (i.e. containing in its pores) a highly activated carbon as disclosed in WO 98/44880.

Foam materials suitable for use in the pathways according to the invention are open cell foam materials being resistant to the aggressive environment in of the visceral contents discharge from the ostomy and not giving rise to liberation of noxious materials. An example of a suitable material is an open-cell polyether foam or an open-cell polyurethane foam, preferably having a thickness of from 0.5 to 10 mm, more preferred from 1 to 5 mm.

DESCRIPTION OF THE PREFERRED EMBODIMENTS

The invention is now explained more in detail with reference to the drawings showing preferred embodiments of the invention. However, it should be understood that the detailed description and specific examples, while indicating preferred embodiments of the invention, are given by way of illustration only, since various changes and modifications within the spirit and scope of the invention will become apparent to those skilled in the art from this detailed description.

Reference is made to FIG. 1, seen from the side facing the user, and FIG. 1A seen from the side facing away from the user, which show a preferred one-piece embodiment of an ostomy appliance of the invention comprising a front wall 98 and a rear wall 99 of a flexible material, said rear wall having an opening 1 into the bag by which waste material can enter the bag. The appliance has an adhesive wafer 2 for adhering to the user's skin. Furthermore, the appliance has a vent 3 on the front wall through which gas may escape from the bag, the opening of said vent being covered by a filter device 4 according to the invention wherein gas inlet and outlet openings are provided in communication with the filter body, the arrangement being so that in use, gas flows through the filter from the inlet opening to the outlet opening, such gas flow being confined to the filter body. The gas inlet opening to the filter is provided with at least two separate and independent closed pathways having inlet openings communicating with the bag and outlet openings communicating with the inlet opening of the filter. The inlet opening of the filter is protected by a microporous hydrophobic and oleophobic membrane covered with a protecting layer in the form of a foam material. The filter device is preferably secured to the wall by welding in a manner known per se.

The hydrophobic and oleophobic membrane reduces the risk of wetting of the filter material and the foam material improves the security against blocking of the inlet opening to the filter. This effect is further enhanced by the independent closed pathways having inlet openings communicating with the interior of the bag and outlet openings communicating with the inlet opening of the filter. Thus, material present in the bag is hampered from entering, at the same time, both pathways leading to the inlet opening of the filter which has been found nearly to eliminate the risk of blocking of the filter by directly pressing the contents of the bag against the inlet opening(s) of the filter e.g. when a lying person turns. e.g. in bed.

Figure 2:
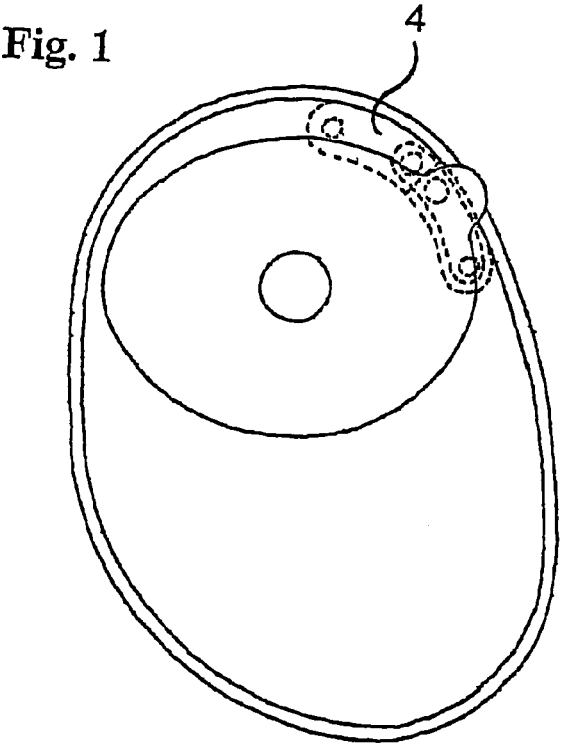
FIG. 2 shows another embodiment of an ostomy appliance of the present invention.
Figure 3:
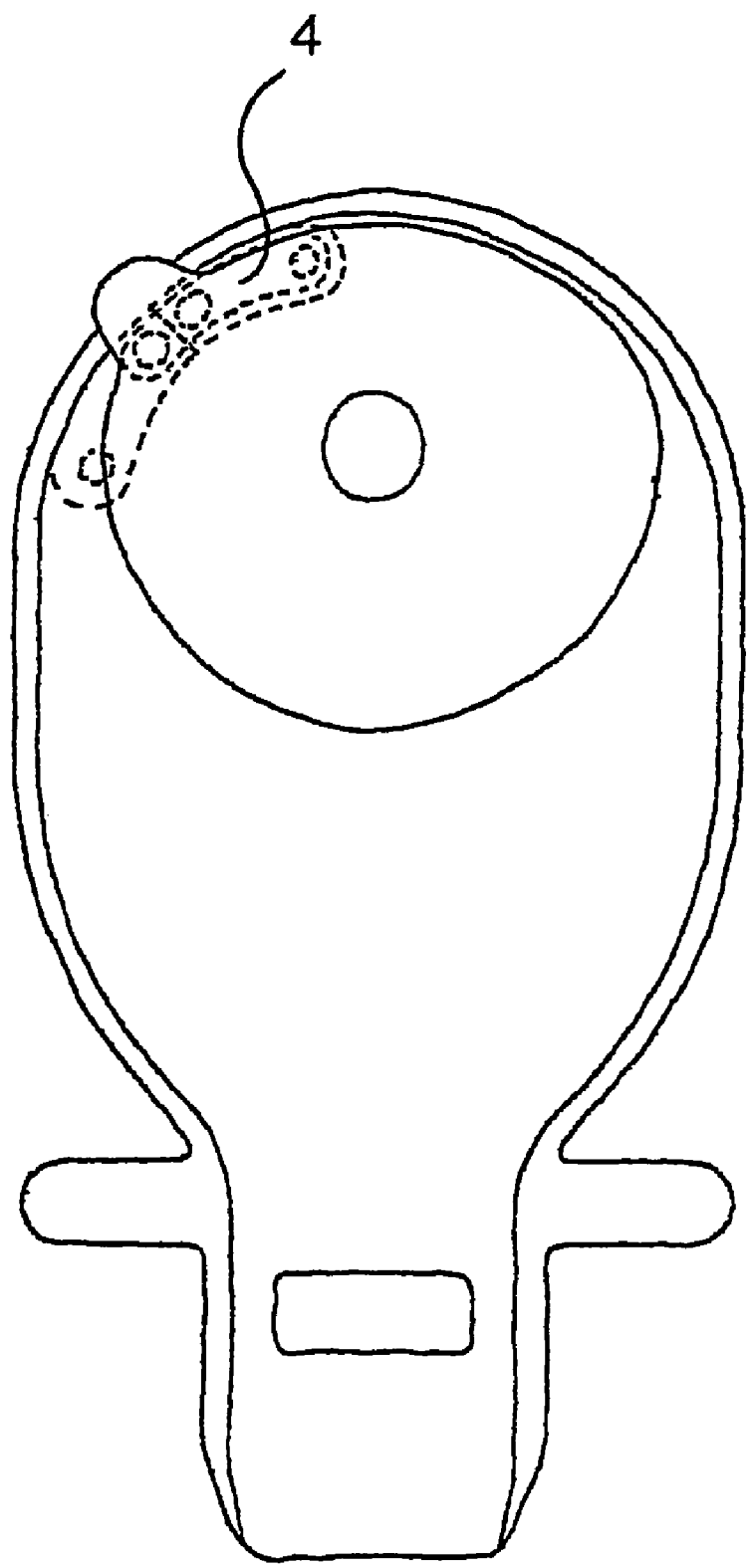
FIG. 3 shows a further embodiment of an ostomy appliance of the present invention.

FIG. 2 shows another embodiment of an ostomy appliance of the invention corresponding to the embodiment of FIG. 1 apart from the placing of the filter device 4 which in this case is placed offset from the vertical centre line of the bag, FIG. 3 shows further embodiment of an ostomy appliance of the invention in the form of an open ostomy appliance which, apart from the filter device 4, corresponds to the collecting bag disclosed in WO 99/66859.

As it will further appear from the embodiments shown in FIGS. 1-3, the essentially circular shape of the top of the bag and the filter device allows for an essentially free placing of the filter device at the most appropriate site place in the top of the bag.

Figure 4:
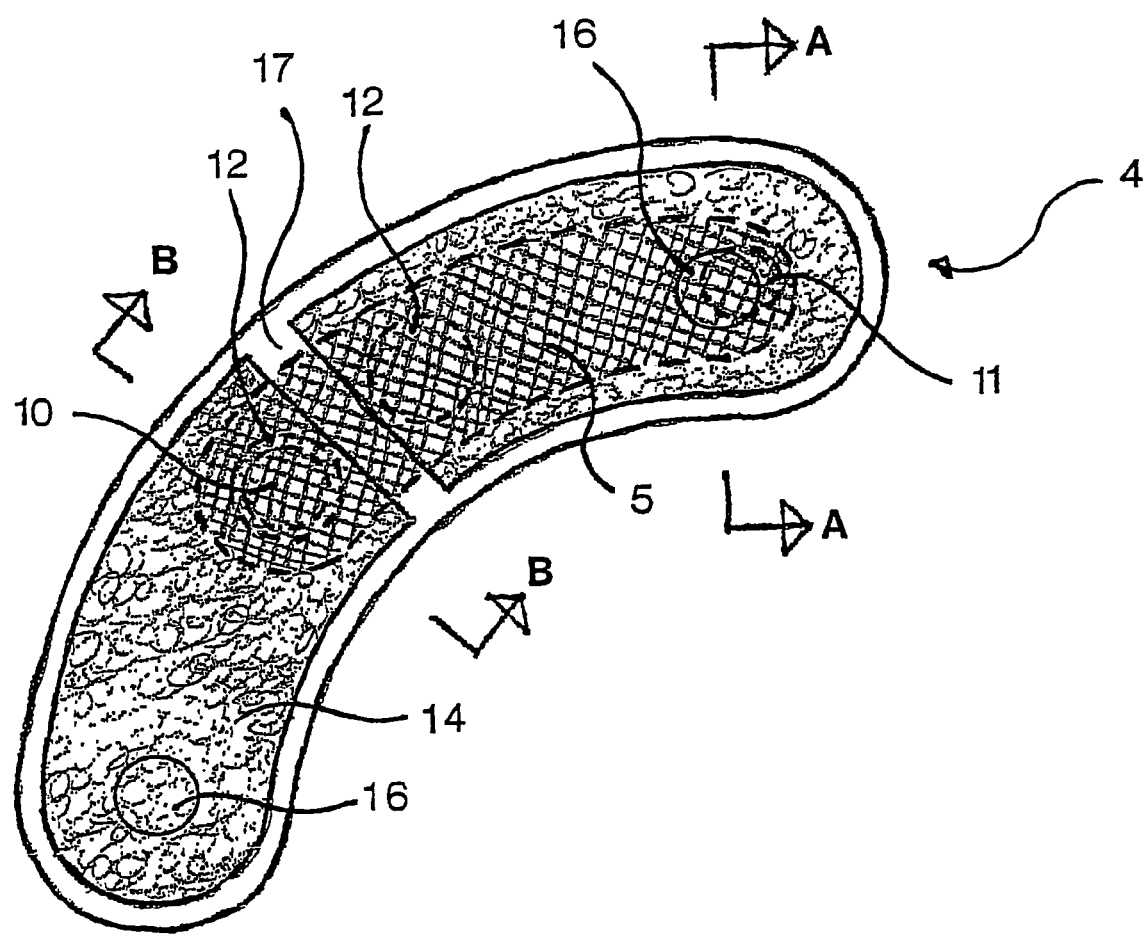
FIG. 4 shows an embodiment a filter device of the invention.
Figures 5, 6:
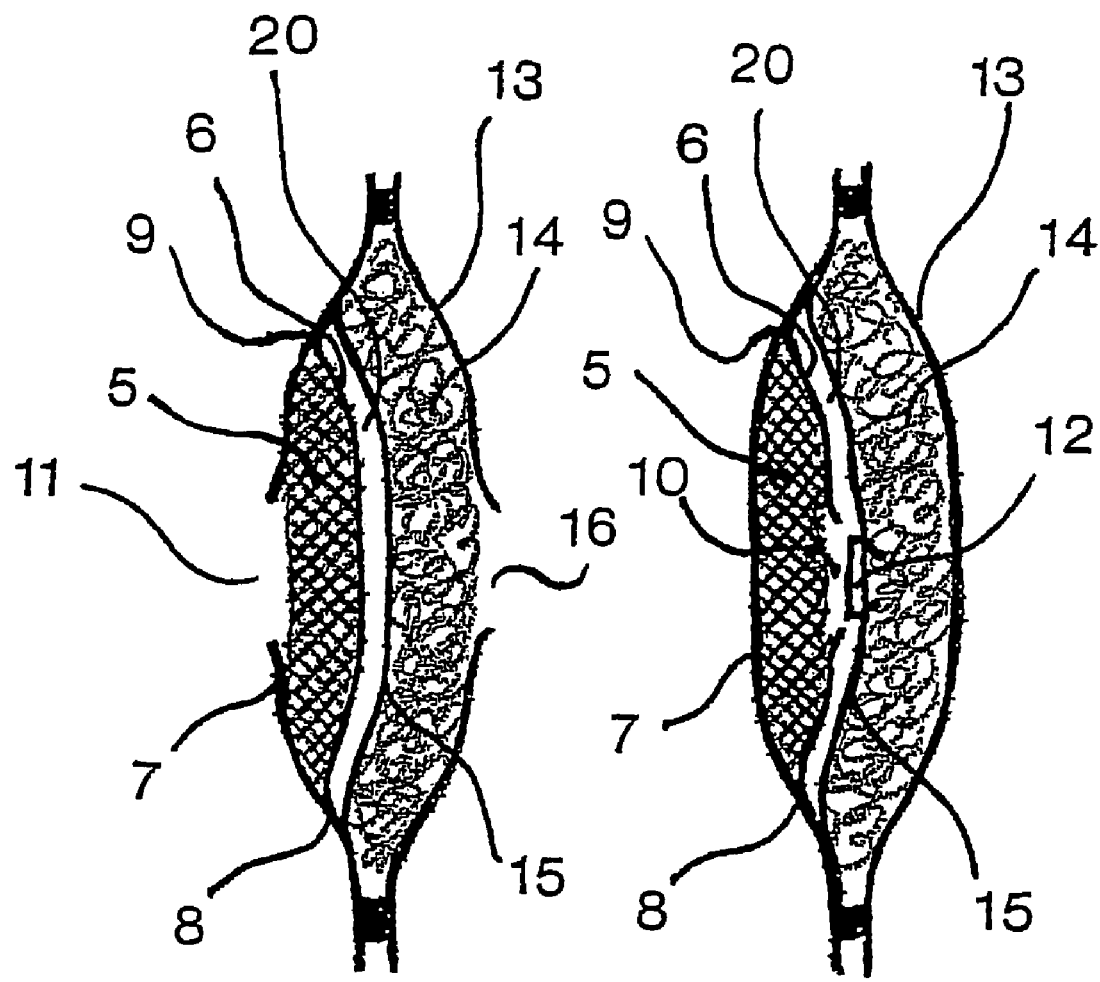
FIG. 5 shows a section along the line A-A of the embodiment of FIG. 4.
FIG. 6 shows a section along the line B-B of the embodiment of FIG. 4.

Reference is now made to FIG. 4 which shows a preferred embodiment of a filter device 4 according to the invention comprising a filter having an elongated, substantially flat filter body 5 of a porous filter material interposed between gas and liquid impervious walls 6,7 as appears from FIGS. 5 and 6 which are sealed to the body along its side edges 8,9 as appears from FIGS. 5 and 6. Gas inlet 10 and outlet 11 openings are provided in communication with the filter body material adjacent to its respective longitudinal end regions, wherein both of the gas and liquid impervious walls are sealed to the upper and lower surfaces of the filter body, the arrangement being so that in use gas flows longitudinally through the filter from the inlet opening to the outlet opening, such gas flow being confined to said filter body and wherein the inlet opening is protected by hydrophobic sheets 12 covering the outlet openings of the closed pathways 18,19 which sheets are microporous oleophobic membranes. The microporous oleophobic membranes are covered with a wall 13 defining a space for placing a foam material 14 to avoid physical blocking which wall is secured to the wall 6 of the filter or to a layer 15 of the ostomy appliance. The wall 13 may be made from a suitable plastic material such as a polyolefin in, e.g. PE, and may be secured above and below the inlet of the filter letting the sides open or may be secured around the opening and have inlet openings 16 allowing gas to enter from the ostomy appliance.

The layer 15 offers a simplification during the production of the filter device as the membrane 12 may be secured to the layer 15 before the final assembling of the filter device. The layer 15 may stretch beyond the limits of the filter and be secured directly to the wall of the ostomy appliance. The wall 15 is sealed to the wall 6 defining a space 20 for collecting the gas passing through the membranes 12 and leading the gas to the inlet opening 10.

Furthermore, there is a sealing member 17 sealing the walls 13 and 15 together between the two membranes 12 and thereby separating the two independent closed pathways 18 and 19. Thus, the gas may flow from the bag through one of the inlet openings 16 through the foam material 14 and the membranes 12 into the space 20 ensuring that all gas passes through the full length of the filter body 5, irrespective of which pathway is used.

Details with respect to the inlet and outlet openings of the various parts of the filter device of this embodiment appear from the sectional views along the lines A-A and B-B shown in FIG. 5 and FIG. 6, respectively.

Figures 7, 8:
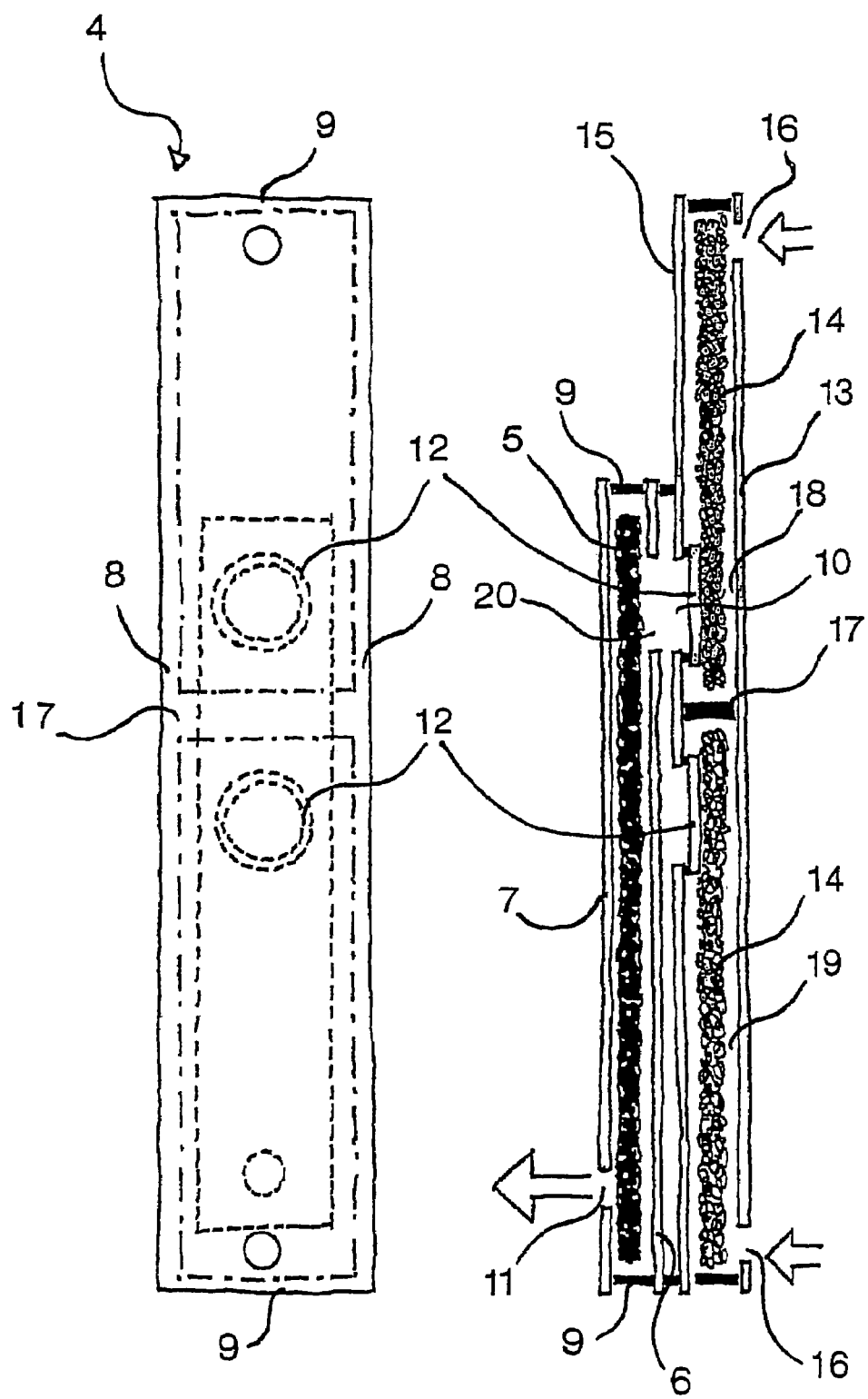
FIG. 7 shows schematically the embodiment of FIG. 4 seen from the inlet side.
FIG. 8 shows an exploded sectional view of the embodiment of FIG. 7.

Reference is made to FIGS. 7 and 8 showing the principle of the embodiment shown in FIG. 4 in the form of a filter device 4 for an ostomy appliance or the like, the filter device comprising a filter having an elongated, substantially flat filter body 5 of a porous filter material interposed between gas and liquid impervious walls 6,7 which are sealed to the body along its side edges 8,9. Gas inlet 10 and outlet 11 openings are provided in communication with the filter body material adjacent to its respective longitudinal end regions, wherein both of the gas and liquid impervious walls are sealed to the upper and lower surfaces of the filter body, the arrangement being so that in use gas flows longitudinally through the filter from the inlet opening to the outlet opening, such gas flow being confined to said filter body and wherein the inlet openings are covered by a hydrophobic sheets 12 which sheets are microporous oleophobic membranes. The microporous oleophobic membranes are covered with a wall 13 defining a space for placing a foam material 14 to avoid physical blocking which wall is secured to the wall 6 of the filter or to a layer 15 of the ostomy appliance. The wall 13 may be made from a suitable plastic material such as a polyolefin in, e.g. PE, and may be secured above and below the inlet of the filter letting the sides open or may be secured around the opening and have inlet openings 16 allowing gas to enter from the ostomy appliance.

The layer 15 offers a simplification during the production of the filter device as the membrane 12 may be secured to the layer 15 before the final assembling of the filter device. The layer 15 may stretch beyond the limits of the filter and be secured directly to the wall of the ostomy appliance. The wall 15 is sealed to the wall 6 defining a space 20 for collecting the gas passing through the membranes 12 and leading the gas to the inlet opening 10. This embodiment enables the use of filter packages having only one inlet opening to the filter body enhancing the efficiency of the filter material.

Furthermore, there is a sealing member 17 sealing the walls 13 and 15 together between the two membranes 12 and thereby separating the two independent closed pathways 18 and 19. Thus, the gas may stream from the bag through one of the inlet openings 16 through the foam material and the membranes 12 into the space 20 ensuring that all gas passes through the full length of the filter body 5, irrespective of which pathway is used.

Materials and Methods

EXAMPLE

Preparation of a filter part of a filter device according to the invention.

A coal package consisting of a filter body of foam impregnated with coal and having a width of 7 mm, a length of 40 mm and a thickness of 2 mm, sealed between two barrier foils comprising the layers EVA, PVDC, EVA and CPE (chlorinated polyethylene), was produced by heat welding the layers around the filter body.

Two hydrophobic and oleophobic membranes were welded over preformed holes placed close to each other in a laminated barrier sheet consisting of EVA, PVDC, EVA and CPE. To the other side of the sheet, the coal package was welded having an inlet hole aligned with one of the membranes only. This entity is defined as the coal/membrane package.

Two pieces of polyether foam with a width of 8 mm, a length of 33 mm and a thickness of 1 mm were placed on a piece of non-woven fabric leaving an area in between free. The non-woven layer was heat welded to the filter package enclosing the foam pieces in two separate compartments each communicating with one of the hydrophobic and oleophobic membranes between the non-woven layer and the coal package. This product is referred to as a "filter package".

The rim of the finished filter package was trimmed into the desired final shape.

The filter may be used together with any ostomy appliance and may be placed on the wall inside or outside the ostomy appliance, on the front side or the back side of the appliance as it is found suitable for the application in question and is suitably heat welded to the wall of a bag.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An ostomy appliance comprising:
a front wall and a rear wall of flexible material forming a bag, the rear wall having an opening into the bag by which waste material can enter the bag and one of the walls having at least one vent through which gas may escape from the bag;
a filter device that covers said vent, said filter device including a filter having first and second walls with a filter body therebetween, a gas inlet opening in said first wall and a gas outlet opening in said second wall both being in communication with said filter body, said gas inlet and outlet openings being arranged such that in use gas flows through the filter from the gas inlet opening to the gas outlet opening, said gas flow being confined to said filter body;
said gas inlet opening of said filter communicating with at least two separate and independent pathway outlet openings of at least two separate and independent closed pathways, respectively, each of said pathway outlet openings being covered by a microporous membrane, said separate and independent closed pathways being defined between said first wall and a further filter device wall having opposing ends sealingly connected to said first wall and a middle portion separated from said first wall by a space to define an area between said sealed ends, said further filter device wall having at least two bag inlet openings separated from one another and communicating with an interior of said bag so that in use, gas flows from the bag inlet openings through said separate and independent closed pathways to the pathway outlet openings, respectively, and then through said gas inlet opening of said filter through said filter body to said gas outlet opening for escape from said appliance; and
a sealing member extending across said space to seal said first wall to said further filter device wall at a point between said opposing ends, said sealing member separating said area into said at least two separate and independent closed pathways and said sealing member being configured to prevent gas that enters one of said closed pathways from a respective one of said pathway inlet openings from egress into the other of said closed pathways.

2. The ostomy appliance as claimed in claim 1, wherein the separate and independent pathways stretch essentially along radii of a circle of reference having a perimeter concentric with the gas inlet opening of the filter and the bag inlet openings of the separate and independent pathways are spaced at an angle of at least 45 degrees.

3. The ostomy appliance as claimed in claim 1 wherein said filter body is elongated and substantially flat and is made of a porous filter material, said gas inlet and outlet openings being provided in communication with the filter body material adjacent to its respective longitudinal end regions, said gas inlet and outlet openings being arranged so that in use gas flows longitudinally through the filter from the gas inlet opening to the gas outlet opening.

4. A deodorising filter device for covering a vent of an ostomy appliance or the like, said filter device comprising:
a filter including a filter body of a porous filter material interposed between first and second walls that are impervious to gas and liquid and which are sealed to the filter body along edges thereof;
a gas inlet opening in said first filter wall and a gas outlet opening in said second filter wall both being in communication with said filter body, said gas inlet and outlet openings being arranged such that in use gas flows through the filter from the gas inlet opening to the gas outlet opening, said gas flow being confined to said filter body;
a further filter device wall separated from said first filter wall by a space to define a pre-filter area and having at least two baa inlet openings communicating with an interior of said baa and with said prefilter area;
a barrier member dividing said pre-filter area into two separate and independent closed pathways each of which communicates with only one of said baa inlet openings and each of which also communicates with said gas inlet opening of said filter through a respective one of two pathway outlet openings so that in use, gas flows from the bag inlet openings through said closed pathways to the pathway outlet openings, respectively, and then through said gas inlet opening of said filter through said filter body to said gas outlet opening for escape from said filter device; and
each of the pathway outlet openings of the separate and independent closed pathways being covered by a microporous membrane.

5. The filter device as claimed in claim 4, wherein said filter body is elongated and substantially flat, said gas inlet and outlet openings being provided in communication with the filter body material adjacent to its respective longitudinal end regions so that in use gas flows longitudinally through the filter from the gas inlet opening to the gas outlet opening, both of the gas and liquid impervious walls being sealed to the upper and lower surfaces of the filter body.

6. The filter device as claimed in claim 4, wherein said gas inlet opening of said filter communicates with two spaced outlet openings of said two closed pathways, respectively, each of said outlet openings being covered by a microporous hydrophobic membrane.

7. The filter device as claimed in claim 6, wherein said membranes are spaced longitudinally from one another with respect to said filter, said barrier member positioned between said membranes.

8. The filter device as claimed in claim 4, wherein the pathways stretch essentially along radii of a circle of reference having a perimeter concentric with the gas inlet opening of the filter, and the bag inlet openings of the pathways are spaced at an angle of at least 45 degrees.

9. The filter device as claimed in claim 6, wherein the membranes covering the two spaced filter inlet openings include a layer of a non-woven material and a layer of an oleophobic PTFE-material.

10. The filter device as claimed in claim 4, wherein a foam material is present in the pathways.

11. The filter device as claimed in claim 5, wherein the filter body has a curved shape.

12. A filter device for covering a vent of an ostomy bag, said filter device comprising:
a filter having a filter body of a porous filter material interposed between first and second walls which are gas and liquid impervious and sealed to the filter body along edges thereof, said filter body being in communication with a gas inlet opening in said first wall and a gas outlet opening in said second wall, said gas inlet and outlet openings being arranged such that in use gas flows through the filter from the gas inlet opening, through the filter body to the gas outlet opening;

said gas inlet opening in said first wall of said filter being covered by a microporous hydrophobic membrane which is covered on a side opposite said filter body by a filter device wall that is spaced from said first filter wall to define an elongated area having a longitudinal length for placing a foam material that covers said membrane and prevents physical blocking thereof; and a sealing member extending transversely to said longitudinal length to seal said first wall to said filter device wall at a point along said longitudinal length of said filter device wall, said sealing member separating said elongated area into two separate and independent closed pathways that are sealed from one another and that have respective pathway inlet openings in said filter device wall separated from one another and each communicating with an interior of said bag, each pathway having a respective pathway outlet communicating with said microporous membrane-covered filter inlet opening, gas entering one of said closed pathways from a respective one of said pathway inlet openings being prevented from egress into the other of said closed pathways by said sealing member.

13. The filter device as claimed in claim 12, wherein a foam material is present in each of said pathways.

14. The filter device as claimed in claim 12, wherein the membrane covering the filter inlet opening includes a layer of a non-woven material and a layer of an oleophobic PTFE-material.

15. The filter device as claimed in claim 12, wherein said filter is elongated and substantially flat, said gas inlet and outlet openings being provided in communication with the filter body adjacent to its respective longitudinal end regions so that in use gas flows longitudinally through the filter from the gas inlet opening to the gas outlet opening, both of the gas and liquid impervious walls being sealed to the upper and lower surfaces of the filter body.

16. The filter device as claimed in claim 12, wherein said filter device is placed inside an ostomy bag such that said gas outlet opening of said filter is aligned with said vent.

17. The filter device as claimed in claim 12, wherein said filter device is placed outside an ostomy bag such that said bag includes two vents and each of said pathway inlet openings is aligned with a respective one of said vents.

18. The filter device as claimed in claim 4, wherein said barrier member is a sealing member that sealingly separates said pathways from one another.

19. The filter device as claimed in claim 18, wherein said sealing member extends across said space transversely to a longitudinal length of said filter device.

20. The filter device as claimed in claim 18, wherein said sealing member joins said first wall to said further filter device wall.

* * * * *